(12) United States Patent
Devi et al.

(10) Patent No.: US 8,445,400 B2
(45) Date of Patent: May 21, 2013

(54) GLYCEROL-BASED SOLID ACID CATALYSTS USEFUL FOR THE ESTERIFICATION OF FATTY ACIDS, A PROCESS AND USE THEREOF

(75) Inventors: Bethala Lakshmi Anu Prabhavathi Devi, Andhra Pradesh (IN); Katkam Nadpi Gangadhar, Andhra Pradesh (IN); Potharaju Seetharamanjaneya Sai Prasad, Andhra Pradesh (IN); Rachapudi Badari Narayana Prasad, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 431 days.

(21) Appl. No.: 12/733,007

(22) PCT Filed: Oct. 26, 2007

(86) PCT No.: PCT/IN2007/000509
§ 371 (c)(1),
(2), (4) Date: Jul. 20, 2010

(87) PCT Pub. No.: WO2009/016646
PCT Pub. Date: Feb. 5, 2009

(65) Prior Publication Data
US 2010/0286421 A1   Nov. 11, 2010

(30) Foreign Application Priority Data
Aug. 1, 2007 (IN) .......................... 1624/DEL/2007

(51) Int. Cl.
*B01J 31/02* (2006.01)
*B01J 31/10* (2006.01)
*C07C 51/493* (2006.01)

(52) U.S. Cl.
USPC ........... 502/168; 502/150; 502/172; 554/174; 554/169; 554/170

(58) Field of Classification Search
None
See application file for complete search history.

(56) References Cited

PUBLICATIONS

Hara, M. et al., A carbon Material as a strong protonic acid, 2004, Angew. Chem. Int. Ed., vol. 43, No. 22, pp. 2995-2958.*
Prager, R.H. et al., Preparation of caroxylate esters of polyhydric alcohols by using a sulfonated charcoal catalyst, 1989, Australian Journal of Chemistry, 42(6), pp. 1003-1005 (1 page abstract).*
Takagaki, A. et al., Esterificatin of higher fatty acids by a novel strong solid acid, 2006, Catalyst Today, vl. 116, pp. 157-161.*

* cited by examiner

*Primary Examiner* — Yate K Cutliff
(74) *Attorney, Agent, or Firm* — Abelman, Frayne & Schwab

(57) ABSTRACT

The present invention provides a novel glycerol-based heterogeneous solid acid catalyst by simultaneous partial carbonization and sulfonation of crude glycerol obtained as a by-product during the biodiesel process. Solid acid catalyst with similar activity is also prepared from glycerol pitch (by-product of fat splitting) and technical grade glycerol. These glycerol-based solid acid catalysts are employed for esterification of fatty acids and fatty acid present in the high and low free fatty acid (FFA) containing vegetable oils like rice bran, karanja and jatropha; fatty acid distillate; deodorizer distillate and acid oil which are being used as raw materials for the preparation of biodiesel. These catalysts are highly active, reusable and simplify the biodiesel process particularly for fatty acids or high FFA containing vegetable oils by replacing the traditional homogeneous mineral acid catalysts.

18 Claims, No Drawings

GLYCEROL-BASED SOLID ACID CATALYSTS USEFUL FOR THE ESTERIFICATION OF FATTY ACIDS, A PROCESS AND USE THEREOF

FIELD OF THE INVENTION

The present invention relates to a novel glycerol-based solid heterogeneous acid catalyst useful for the esterification of fatty acids. The present invention also relates to a process for the preparation of glycerol-based solid heterogeneous acid catalyst. The present invention further relates to a process for the esterification of fatty acids or fatty acids present in vegetable oils and animal fats using glycerol-based solid heterogeneous acid catalyst. The glycerol used in the preparation of glycerol-based solid heterogeneous acid catalyst is selected from crude glycerol obtained as a by-product during biodiesel process, glycerol pitch obtained as by-product of fat splitting and technical grade glycerol. The vegetable oils and animals fats with high and low free fatty acid (FFA) used in esterification are rice bran, karanja and jatropha; and tallow fat; fatty acid distillate resulting in deacidification of vegetable oils and fatty acid present in acid oil and deodorizer distillate with alcohols.

BACKGROUND OF THE INVENTION

Biodiesel is generally prepared by the transesterification of natural oil or fat of vegetable or animal origin. The transesterification is carried out by acid or base catalysis. As the rate of reaction of the base catalyst is much faster than the acid catalyst, base catalysts are used, most often, commercially. For an alkali catalyzed transesterification, the glycerides and alcohol must be free from water and free fatty acids. Some of the natural oils or fats contain considerable amounts of free fatty acids, which interfere during the transesterification process. These free fatty acids are to be converted into their corresponding esters before transesterification. Thus, esterification forms an essential step in the production of biodiesel in case of oils containing free fatty acids.

Esterification is a very widely employed reaction in the organic process industry. Esters fall under a wide category ranging from aliphatic to aromatic with various multifunctional groups. Organic esters are most frequently used as plasticizers, solvents, perfumery and flavor chemicals and also as precursors to a gamut of pharmaceuticals, agrochemicals and other fine chemicals. Esterification reactions are conventionally carried out homogeneously using mineral acids such as sulfuric acid or Lewis acids as catalysts. These acids are corrosive and the excess acid has to be neutralized after the reaction, leaving considerable amount of salts to be disposed off into the environment.

Process for the preparation of biodiesel from low FFA and high quality oils may not be so difficult. The main challenge of the biodiesel technology is handling the multi feed stocks with high FFA. In case of high FFA oils, initially the fatty acid has to be esterified using acid catalyst like sulfuric acid followed by neutralization of the catalyst before going for alkali-based transesterification. The major problem of acid catalyst is the formation of salts during neutralization and also conversions are not very high like transesterification. This process involves high consumption of energy and the separation of the catalysts from the homogenous reaction mixtures is expensive and chemically wasteful.

Over 15 million tons of sulfuric acid is annually consumed as "unrecyclable catalyst, which requires expensive and inefficient separation of the catalyst from homogenous reaction mixtures for the production of industrially important chemicals, thus resulting in a huge waste of energy and large amounts of waste products. The green approach to chemical processes has stimulated the use of recyclable strong heterogeneous solid acids as replacement for such non-recyclable liquid acid catalysts. Tightening legislation on the emission of hazardous pollutants is driving the industry toward the implementation of innovative clean technology including the use of alternative heterogeneously catalyzed processes. The use of heterogeneous catalysts for these reactions offer several intrinsic advantages over their homogeneous counterparts like insolubility in the product i.e. ease of product separation, catalyst reuse and process advantages through reactor operation in continuous flow versus batch configuration. However, to maintain economic viability, a suitable heterogeneous catalyst not only minimizes the production of waste, but also exhibit activities and selectivity comparable or superior to the existing homogeneous catalysts.

Solid acid catalysts are of increasing importance for esterification in the production of bulk and fine chemicals. The use of solid catalysts offers an alternative to mineral acids and has received a lot of attention in the past years. Though, considerable amount of literature exists on esterification of simple aliphatic and aromatic acids using various solid acid catalysts like the resins, zeolites, heteropoly acids like tungstophosphoric acid and its amine salts and superacids like sulfated zirconia and niobium acid, only a few reports can be seen on the esterification of fatty acids. These catalysts have low densities of effective acid sites and thus cannot achieve adequate performance in acid-catalyzed reactions in the presence of water as replacement for homogeneous Bronsted acids in esterification [B. Y. Giri et al., Cat. Commu. 6, p. 788 (2005); S. Inagaki et al., Nature, 416, p. 304 (2002); K. Wilson et al., Applied Cat. A Gen. 228, p. 27 (2002); E. Cano-Serrano et al., Chem. Commu. 247, p. 246 (2003)]. These heterogeneous catalysts also have some drawbacks such as tedious preparation, leaching of the catalysts in to the reaction medium, change of active sites in the structure of the catalyst after reaction and hence not reusable and the starting materials are also expensive.

Michikazu Hara et al., [Angew Chem. Int. Ed., 43, p. 2955-2958 (2004)] reported the preparation of a solid acid catalyst by sulfonating naphthalene after carbonization at 200 to 250 deg C. However, it is a soft material and its aromatic molecules are leached out during liquid-phase reactions above 100 deg. C or when higher fatty acids are used as surfactants, so its catalytic activity is rapidly lost. The preparation of the reported solid catalyst was very tedious like heating the organic material with sulfuric acid at very high temperatures of 523 K under a flow of nitrogen for 15 hr in excess amounts of sulphuric acid (1:20 wt/vol). Excess sulfuric acid was removed from the product by vacuum distillation at the same temperature for 5 hr, which resulted in a black solid. The same authors have filed a European patent (EP 1,667,167, 2006) wherein the preparation of sulfonated amorphous carbon catalyst was reported from aromatic hydrocarbons such as benzene, naphthalene, anthracene, peryrene and coronene. However, a molar ratio of 1:6-36 of organic compound to sulfuric acid was used. In a separate US patent application (US 20060276668) the same authors disclosed the preparation of sulfonated composite solid acid catalyst containing the amorphous carbon, prepared by the above method from polycyclic aromatic hydrocarbons obtained by condensing two or more aromatic rings or tar, pitch, fuel oil or asphalt and incorporated a solid carbon component like carbon black, acetylene black, activated carbon, carbon nano tube or fullerene at high temperatures up to 450.degree. C. In this patent large amounts of sulfuric acid was also used, which necessitated removal of excess sulfuric acid by vacuum distillation. Masakakazu Toda et al., in their communication [Nature, 438, p 178 (2005); Catalysis Today, 116, p 157 (2006)] reported the preparation of another solid acid catalyst by sulfonating incompletely carbonized natural organic materials such as sugar, starch or cellulose. The preparation of this catalyst is also very tedious, involving heating of D-glucose or sucrose powder at 400.degree. C. under N.sub.2 flow for 15 hr to get the brown black solid which was further sulfonated by heating with more amount of concentrated sulfuric acid or fuming sulfuric acid (1:20 wt/vol) at 150.degree. C. under N.sub.2 for 15 h followed by hot water wash, which resulted in a black solid acid catalyst.

OBJECTIVES OF THE INVENTION

The main object of the present invention is to provide a novel glycerol-based solid heterogeneous acid catalyst useful for the esterification of fatty acids.

Another object of the present invention is to provide a process for the preparation of glycerol-based solid heterogeneous acid catalyst.

Yet another object of the present invention is to provide a catalyst prepared from crude glycerol, a by-product of biodiesel without any pre-treatment, thereby enhancing the value of glycerol and the economy of biodiesel industry.

Still another object of the present invention is to provide a process for the esterification of fatty acids or fatty acid present in vegetable oils, animal fats, fatty acid distillate, acid oil and deodorizer distillate with alcohols using glycerol-based solid heterogeneous acid catalyst for the production of biodiesel.

SUMMARY OF THE INVENTION

Accordingly the present invention provides a novel glycerol based heterogeneous solid acid catalyst useful for esterification of fatty acids or fatty acids present in vegetable oils and animal fats and having the following characteristics:
  i. molecular formula $CH_{0.53-0.87}S_{0.015-0.03}O_{0.035-0.51}$;
  ii. acid density in the range of 1.6-4.6 mMol/g;
  iii. surface area of 2-12.6 m$^2$/g;
  iv. insoluble in water and organic solvent like chloroform, hexane, pyridine and N,N-dimethylformamide and
  v. reusable.

In an embodiment of the present invention the glycerol based heterogeneous solid acid catalyst is useful for the esterification of fatty acids, high and low free fatty acids (FFA) of vegetable oils and animal fats selected from the group consisting of rice bran, karanja, jatropha, sunflower oil deodorizer distillate, fatty acid distillate and tallow fat.

Accordingly the present invention provides a novel glycerol based heterogeneous solid acid catalyst useful for esterification of fatty acids or fatty acids present in vegetable oils and animal fats and having the following characteristics:
  i. molecular formula $CH_{0.53-0.87}S_{0.015-0.03}O_{0.035-0.51}$;
  ii. acid density in the range of 1.6-4.6 mMol/g;
  iii. surface area of 2-12.6 m.sup.2/g;
  iv. insoluble in water and organic solvent like chloroform, hexane, pyridine and N,N-dimethylformamide and
  v. reusable.

and a process for the preparation of said catalyst, said process comprises simultaneous partial carbonization and sulfonation of glycerol by reacting it with concentrated or fuming sulphuric acid, at a temperature in the range of 200-300° C., under the stream of N$_2$ gas or dry air, for a period till the reaction mixture becomes black powder, cooling the resultant black powder to a temperature of 20-30° C. and washing it with hot water till neutralization of wash water to neutral pH, followed by washing and drying the resultant product, at a temperature of 110-130° C. to obtain the desired heterogeneous solid acid catalyst.

In yet another embodiment the glycerol used is selected from the group consisting of technical grade glycerol, crude glycerol obtained as byproduct during biodiesel process and glycerol pitch obtained as byproduct of fat splitting.

In yet another embodiment the ratio of glycerol to sulphuric acid used is about 1:4 (w/w).

In yet another embodiment the heterogeneous acid catalyst obtained has the following characteristics:
  i. molecular formula $CH_{0.53-0.87}S_{0.015-0.03}O_{0.035-0.51}$;
  ii. acid density in the range of 1.6-4.6 mMol/g;
  iii. surface are of 2-12.6 m$^2$/g;
  iv. insoluble in water and organic solvent like chloroform, hexane, pyridine and N,N-dimethylformamide, and
  v. reusable.

The present invention further provides a process for the esterification of vegetable oil free fatty acids using glycerol based heterogeneous solid acid catalyst which comprises reacting vegetable oil with 3-85% free fatty acid (FFA) with alcohol in the presence of solid acid catalyst, at a temperature of 35-90° C., for a period of 1-12 hours to obtain the resultant corresponding fatty acid esters.

In yet another embodiment the fatty acid moiety used contains any carbon atom number up to 24.

In yet another embodiment the alcohol used is selected from methanol, ethanol and isopropanol.

In yet another embodiment the molar ratio of fatty acid to alcohol used is in the range of 1:1 to 1:30.

In yet another embodiment the reaction temperature used is preferably in the range of 60-75° C.

In yet another embodiment the glycerol based solid acid catalyst used is 2-20% of the free fatty acid present in the vegetable oil feed stock.

In yet another embodiment the reaction time used for esterification is preferably in the range of 3-5 hours.

In yet another embodiment the catalyst used is employed either in batch or continuous process of esterification.

In yet another embodiment the catalyst used is recyclable for at least 10 times without any leaching in the reaction system.

In yet another embodiment the heterogeneous acid catalyst used has the following characteristics:
  i. molecular formula $CH_{0.53-0.87}S_{0.015-0.03}O_{0.035-0.51}$;
  ii. acid density in the range of 1.6-4.6 mMol/g;
  iii. surface are of 2-12.6 m$^2$/g;
  iv. insoluble in water and organic solvents selected from the group consisting of chloroform, hexane, pyridine, N,N-dimethylformamide, and
  v. reusable.

In yet another embodiment the yield of % conversion esterification of alcohol is in the range of 45-99%.

DETAILED DESCRIPTION OF THE INVENTION

Herein, we report the synthesis of a glycerol-based solid acid catalyst with a high density of sulfonic acid groups (SO$_3$H) from cheaper waste products like crude glycerol obtained as a by-product during biodiesel process and glycerol pitch, a by-product of fat splitting and technical grade glycerol.

In the present invention, glycerol-based solid acid catalyst is obtained in a single pot reaction by simultaneous partial carbonization and sulfonation of the above raw materials. The reaction was very rapid and this solid heterogeneous acid catalyst consists of small polycyclic aromatic carbon sheets with attached $SO_3H$ groups to afford a highly stable solid with a high density of active sites along with high-performance catalytic activity towards the esterification of fatty acids into alkyl esters (biodiesel). The chemical formula of the glycerol-based solid acid catalyst is different from that of sugar-based solid acid catalyst. Acid density and surface area of the glycerol-based solid acid catalyst is superior to that of sugar-based catalyst. The comparative data is provided in Table 1.

TABLE 1

Properties of the glycerol-based solid acid catalysts in comparison to sugar-based solid acid catalyst.

| Property | Sugar-based solid acid catalyst [Nature, 438, p 178 (2005); Catalysis Today, 116, p 157 (2006)] | Glycerol-based solid acid catalyst (Present invention) |
|---|---|---|
| Chemical formula | $CH_{0.29-0.45}S_{0.01-0.03}O_{0.39-0.45}$ | $CH_{0.53-0.87}S_{0.015-0.03}O_{0.35-0.51}$ |
| Acid density | 1.4-2.5 mmol/g | 1.6-4.6 mmol/g |
| Surface area | 1-2 $m^2/g$ | 2-12.6 $m^2/g$ |

In an embodiment of the present invention an efficient process is developed for producing glycerol-based heterogeneous solid acid catalysts from crude glycerol, a by-product of biodiesel process, glycerol pitch (by-product of fat splitting) and technical grade glycerol and the resultant solid acid catalysts are employed for esterification of fatty acids or fatty acid present in the high and low FFA vegetable oils and animal fats like rice bran, karanja and jatropha; fatty acid distillate, deodorizer distillate, acid oil and tallow fat which are being used as raw materials for the preparation of biodiesel.

The present invention describes an effective, novel, stable, reusable and cheaper glycerol-based sulfonated solid acid catalyst by using crude glycerol, a by-product of biodiesel process, glycerol pitch and technical grade glycerol involving simultaneous partial carbonization and sulfonation with concentrated sulfuric acid or fuming sulfuric acid conducted in a stream of an inert gas or dry air. The resultant solid acid catalysts are used for the preparation of biodiesel from fatty acids, high or low FFA containing oils and fats like jatropha, karanja and rice bran and tallow, fatty acid distillate, deodorizer distillate and acid oil.

The glycerol-based solid acid catalyst can be prepared easily in large scale in commercially viable manner. This catalyst can replace any type of sulfuric acid catalyzed esterification reactions with several advantages like easy work up of the products by simple filtration of the catalyst, recyclable several times with out loosing the activity.

The glycerol-based solid acid catalyst with the amorphous nature having sulfonate groups is produced by heat treatment of the above feed stocks in concentrated sulfuric acid or fuming sulfuric acid from 0.5 to 6 times (by wt.) of the feed stock, preferably 2 to 4 times, conducted in a stream of an inert gas or dry air at a temperature of 100 degree C. to 300 degree C., preferably 150 to 250 degree C., for 10 minutes to 3 hours, preferably 15 minutes to 30 minutes.

The glycerol-based solid acid catalysts have an acid strength expressed in terms of mmol/g in the range of 1.6 to 4.6 with a surface area of 2-12.6 $m^2/g$.

The elemental analysis of glycerol-based solid acid catalysts revealed that its provisional molecular composition expressed as $CH_xS_yO_z$ where the values of x, y and z vary in the range of 0.53 to 0.87, 0.015 to 0.03 and 0.35 to 0.51 respectively.

The glycerol-based solid acid catalysts are insoluble in water and organic solvents like methanol, ethanol, chloroform, benzene, hexane, pyridine, N, N-dimethylformamide etc.

The glycerol-based solid acid catalysts are employed for esterification of fatty acid, fatty acid present in the high and low FFA vegetable oils and animal fat, or fatty acid distillates, or acid oil or fatty acid mixtures in which the fatty acid moieties are up to $C_{24}$ and alcohol such as methanol, ethanol, isopropanol etc., for the production of alky esters which are useful as biodiesel. The molar ratio of fatty acid to alcohol employed for esterification is in the range of 1:1 to 1:30, preferably 1:1 to 1:10 to convert all the free fatty acid to alkyl esters in a temperature is in the range of from 35 deg. C. to 90 degree C., preferably 55 to 80 degree C. for about 1 to 12 hours, preferably 3 to 5 hours in presence 2 to 20%, preferably 5 to 15% of the free fatty acid present in the feed stock as solid catalyst.

The following examples are intended only to further illustrate the invention and are not intended to limit the scope of the invention as defined by the claims.

EXAMPLE 1

A mixture of crude glycerol (10 g) obtained during biodiesel process and Con. $H_2SO_4$ (40 g) was heated at 250° C. in a stream of nitrogen gas for 15 min till the reaction mixture becomes black powder. Then the material was cooled to room temperature and washed with hot water till the wash water becomes neutral to pH. The solid was filtered and dried in the oven at 120° C. to get the glycerol based solid acid catalyst (4.8 g). The molecular formula of this catalyst was found to be $CH_{0.53}S_{0.017}O_{0.42}$ with 4.6 m mol/g of acid density and 2 $m^2/g$ of surface area. The activity of the catalyst was evaluated for the esterification of sunflower oil fatty acids (10 g) with methanol (10 ml) and the catalyst (2 gm) at 60-62° C. for 4 hr to get fatty acid methyl esters in 99.5% conversion.

EXAMPLE 2

A mixture of technical grade glycerol (10 g) and Con. $H_2SO_4$ (40 g) was heated at 200° C. in a stream of nitrogen gas for 15 min till the reaction mixture becomes black powder. Then the material was cooled to room temperature and washed with hot water till the wash water becomes neutral to pH. The solid was filtered and dried in the oven at 120° C. to get the glycerol based solid acid catalyst (4.9 g). The molecular formula of this catalyst was found to be $CH_{0.74}S_{0.02}O_{0.51}$ with 1.6 mmol/g of acid density and 12.6 $m^2/g$ of surface area. The activity of the catalyst was evaluated for the esterification of sunflower oil fatty acids (10 g) with methanol (10 ml) and the catalyst (1 g) at 60-62° C. for 4 hr to get fatty acid methyl esters in 99.4% conversion.

EXAMPLE 3

A mixture of glycerol pitch (10 g) and Con. $H_2SO_4$ (40 g) was heated at 300° C. in a stream of nitrogen for 15 min till the reaction mixture becomes black powder. Then the material was cooled to room temperature and washed with hot water till the wash water becomes neutral to pH. The solid was filtered and dried in the oven at 120° C. to get the glycerol pitch based solid acid catalyst (4.9 g). The molecular formula of this catalyst was found to be $CH_{0.87}S_{0.024}O_{0.39}$; with 1.9 mmol/g of acid density and 8.66 m$^2$/g of surface area. The activity of the catalyst was evaluated for the esterification of sunflower oil fatty acids (10 g) with methanol (5 ml) and the catalyst (2 g) at 60-62° C. for 5 hr to get fatty acid methyl esters in 98% conversion.

EXAMPLE 4

The solid acid catalyst prepared as described in Example 1 was employed for the esterification of sunflower oil fatty acids to its methyl esters. Sunflower oil fatty acids (10 g) were taken in methanol (5 ml) along with solid acid catalyst (2 g) and refluxed the contents at 60-62° C. for 3 hr to get sunflower oil fatty acid methyl esters in 97.5% conversion.

EXAMPLE 5

The solid acid catalyst prepared as described in Example 1 was employed for the esterification of free fatty acid present in high FFA containing vegetable oil to its methyl esters. Rice bran oil with 35% FFA (10 g) was taken in methanol (10 ml) along with solid acid catalyst (0.7 g) and refluxed the contents at 60-62° C. for 5 hr to convert the free fatty acid to fatty acid methyl esters in 98.0% conversion.

EXAMPLE 6

The solid acid catalyst prepared as described in Example 1 was employed for the preparation of methyl esters of fatty acid distillate. Rice bran oil fatty acid distillate with 80% FFA (10 g) was taken in methanol (3 ml) along with solid acid catalyst (1.6 g) and refluxed the contents at 60-62° C. for 5 hr to convert the free fatty acid to fatty acid methyl esters in 98.5% conversion.

EXAMPLE 7

The solid acid catalyst prepared as described in Example 2 was employed for the esterification of fatty acid present in deodorizer distillate to methyl esters. Soybean oil deodorizer distillate with 70% FFA (10 g) was taken in methanol (3 ml) along with solid acid catalyst (1.4 g) and refluxed the contents at 60-62° C. for 6 hr to convert the free fatty acid present in deodorizer distillate to fatty acid methyl esters in 99.5% conversion.

EXAMPLE 8

The solid acid catalyst prepared as described in Example 3 was employed for the esterification of acid oil to its methyl esters. Pre-treated rice bran oil acid oil with 63% FFA (10 g) was taken in methanol (10 ml) along with solid acid catalyst (1.26 g) and refluxed the contents at 60-62° C. for 4 hr to convert the free fatty acid present in rice bran oil acid oil to fatty acid methyl esters in 98.6% conversion.

EXAMPLE 9

A mixture of technical grade glycerol (10 g) and Con. $H_2SO_4$ (10 g) was heated at 300° C. for 15 min till the reaction mixture becomes black powder. Then the material was cooled to room temperature and washed with hot water till the wash water becomes neutral to pH. The solid was filtered and dried in the oven at 120° C. to get the glycerol based solid acid catalyst (3.5 g). The activity of the catalyst was evaluated for the esterification of sunflower oil fatty acids (10 g) with methanol (10 ml) and the catalyst (2 g) at 60-62° C. for 12 hr to get fatty acid methyl esters in 75% conversion.

EXAMPLE 10

A mixture of technical grade glycerol (10 g) and Con. $H_2SO_4$ (15 g) was heated at 100° C. for 180 min till the reaction mixture becomes black powder. Then the material was cooled to room temperature and washed with hot water till the wash water becomes neutral to pH. The solid was filtered and dried in the oven at 120° C. to get the glycerol based solid acid catalyst (4.0 g). The activity of the catalyst was evaluated for the esterification of sunflower oil fatty acids (10 g) with methanol (10 ml) and the catalyst (2 g) at 60-62° C. for 8 hr to get fatty acid methyl esters in 80% conversion.

EXAMPLE 11

The solid acid catalyst prepared as described in Example 1 was employed for the preparation of sunflower oil fatty acid methyl esters. Sunflower oil fatty acids (10 g) were taken in methanol (1 ml) along with solid acid catalyst (2 g) and refluxed the contents at 60-62° C. for 4 hr to get fatty acid methyl esters in 98% conversion.

EXAMPLE 12

The solid acid catalyst prepared as described in Example 3 was employed for the preparation of sunflower oil fatty acid methyl esters. Sunflower oil fatty acids (10 g) were taken in methanol (10 ml) along with solid acid catalyst (2 g) and stirred the contents at room temperature (~35° C.) for 12 hr to get fatty acid methyl esters in 45% conversion.

EXAMPLE 13

The solid acid catalyst prepared as described in Example 2 was employed for the preparation of sunflower oil fatty acid ethyl esters. Sunflower oil fatty acids (10 g) were taken in ethanol (10 ml) along with solid acid catalyst (2 g) and refluxed the contents at 70-72° C. for 4 hr to get fatty acid ethyl esters in 99.2% conversion.

EXAMPLE 14

The solid acid catalyst prepared as described in Example 1 was employed for the preparation of sunflower oil fatty acid isopropyl esters. Sunflower oil fatty acids (10 g) were taken in isopropanol (10 ml) along with solid acid catalyst (2 g) and refluxed the contents at 80-82° C. for 4 hr to get fatty acid isopropyl esters in 98.5% conversion.

EXAMPLE 15

The solid acid catalyst prepared as described in Example 3 was employed for the esterification of sunflower oil fatty acids to its methyl esters. Sunflower oil fatty acids (10 g) were taken in methanol (10 ml) along with solid acid catalyst (0.2 g) and refluxed-the contents at 60-62° C. for 12 hr to get fatty acid methyl esters in 55.0% conversion.

EXAMPLE 16

The solid acid catalyst prepared as described in Example 1 was employed for the esterification of sunflower oil fatty acids to its methyl esters. Sunflower oil fatty acids (10 g) were taken in methanol (10 ml) along with solid acid catalyst (0.5 g) and refluxed the contents at 60-62° C. for 8 hr to get fatty acid methyl esters in 90.3% conversion.

EXAMPLE 17

The solid acid catalyst prepared as described in Example 2 was employed for the preparation of methyl esters of palmitic acid. Palmitic acid (10 g) was taken in methanol (10 ml) along with solid acid catalyst (2 g) and refluxed the contents at 60-62° C. for 4 hr to get fatty acid methyl esters in 99.3% conversion. The catalyst did not loose its activity even after reusing the same catalyst for the preparation of methyl esters of palmitic acid for 10 times.

EXAMPLE 18

The solid acid catalyst prepared as described in Example 2 was employed for the esterification of free fatty acids present in jatropha oil to its methyl esters. Jatropha oil with 5% FFA (100 g) was taken in methanol (50 ml) along with solid acid catalyst (1 g) and refluxed the contents at 60-62° C. for 3 hr to convert the free fatty acid to fatty acid methyl esters in 99.5% conversion.

EXAMPLE 19

The solid acid catalyst prepared as described in Example 1 was employed for the esterification of free fatty acids present in karanja oil to its methyl esters. Karanja oil with 3% FFA (100 g) was taken in methanol (50 ml) along with solid acid catalyst (0.6 g) and refluxed the contents at 60-62° C. for 2 hr to convert the free fatty acid present in karanja oil to fatty acid methyl esters in 98.5% conversion.

EXAMPLE 20

The solid acid catalyst prepared as described in Example 3 was employed for the esterification of free fatty acids present in the synthetic mixture of sunflower oil and 10% sunflower oil fatty acids to its methyl esters. A synthetic mixture of sunflower oil and containing 10% sunflower oil fatty acids (50 g) were taken in methanol (50 ml) along with solid acid catalyst (1 g) and refluxed the contents at 60-62° C. for 4 hr to convert the free fatty acid present in sunflower oil to fatty acid methyl esters in 98.5% conversion.

EXAMPLE 21

The solid acid catalyst prepared as described in Example 1 was employed for the esterification of free fatty acids present in the synthetic mixture of sunflower oil and 30% sunflower oil fatty acids to its methyl esters. A synthetic mixture of sunflower oil and 30% sunflower oil fatty acids (50 g) were taken in methanol (50 ml) along with solid acid catalyst (3 g) and refluxed the contents at 60-62° C. for 5 hr to convert the free fatty acid present in sunflower oil to fatty acid methyl esters in 99.2% conversion.

EXAMPLE 22

The solid acid catalyst prepared as described in Example 1 was employed for the esterification of sunflower oil fatty acids to its methyl esters. Sunflower oil fatty acids (10 g) were taken in methanol (10 ml) along with solid acid catalyst (5 g) and refluxed the contents at 60-62° C. for 1 hr to get fatty acid methyl esters in 98.5% conversion.

EXAMPLE 23

A mixture of technical grade glycerol (10 g) and fuming sulfuric acid (40 g) was heated at 200° C. in a stream of nitrogen gas for 15 min till the reaction mixture becomes black powder. Then the material was cooled to room temperature and washed with hot water till the wash water becomes neutral to pH. The solid was filtered and dried in the oven at 120° C. to get the glycerol based solid acid catalyst (4.5 g). The activity of the catalyst was evaluated for the esterification of sunflower oil fatty acids (10 g) with methanol (10 ml) and the catalyst (1 g) at 60-62° C. for 4 hr to get fatty acid methyl esters in 99.6% conversion.

EXAMPLE 24

The solid acid catalyst prepared as described in Example 1 was employed for the esterification of free fatty acids present in tallow fat (animal fat) to its methyl esters. Tallow fat oil with 8% FFA (100 g) was taken in methanol (50 ml) along with solid acid catalyst (1 g) and refluxed the contents at 60-62° C. for 3 hr to convert the free fatty acid to fatty acid methyl esters in 99.5% conversion.

ADVANTAGES OF THE INVENTION

1. The glycerol-based heterogeneous solid acid catalyst is prepared from crude glycerol, a by-product of biodiesel without any pre-treatment. This application enhances the value of glycerol, which indirectly enhances the economics of biodiesel industry.
2. Another feedstock for the preparation of solid acid catalyst is glycerol pitch, which is a low value by-product of fat splitting process. As fat splitting industry is facing several problems to dispose the glycerol pitch, this application may enhance the value to glycerol pitch.
3. Technical grade glycerol is also used for the value addition through the preparation of glycerol-based solid acid catalyst.
4. The preparation of glycerol-based heterogeneous solid acid catalyst is carried out simultaneously by partial carbonization and sulfonation in a single pot reaction and the resultant solid acids contain more acid density and hydrogen moieties.
5. The preparation of solid heterogeneous acid catalyst is very simple compared to reported carbon based or other heterogeneous catalysts.
6. The solid acid catalyst is insoluble in water and organic solvents like chloroform, methanol, ethanol, benzene, hexane, pyridine, N,N-dimethylformamide etc., The catalyst is also not soluble in fatty acids and vegetable oils.
7. There was no loss of activity of —$SO_3H$ during the esterification process even after recycling the catalyst for several times.
8. The glycerol-based solid acid catalyst is not water sensitive and esterification of fatty acid is completed even in presence of liberated water.
9. The glycerol-based solid acid catalyst can be employed either in batch or continuous process of esterification.

The invention claimed is:
1. A glycerol based heterogeneous solid acid catalyst useful for the esterification of fatty acids having the following characteristics:

i. molecular composition $CH_{0.53-0.87}S_{0.015-0.03}O_{0.035-0.51}$;
ii. acid density in the range of 1.6-4.6 mMol/g;
iii. surface area of 2-12.6 m²/g;
iv. insoluble in water and organic solvent; and
v. reusable.

2. The catalyst according to claim 1 for the esterification of fatty acids, high and low free fatty acids (FFA) containing vegetable oils and animal fats selected from the group consisting of rice bran, karanja, jatropha oils, tallow fat, vegetable oil deodorizer distillate, acid oil and fatty acid distillate by contacting with an alcohol in the presence of the solid acid catalyst to obtain the resultant corresponding fatty acid esters.

3. A process for the preparation of a glycerol based heterogeneous solid acid catalyst for the esterification of fatty acids and fatty acid containing vegetable oils and animal fats having the following characteristics:
  i. molecular composition $CH_{0.53-0.87}S_{0.015-0.03}O_{0.035-0.51}$;
  ii. acid density in the range of 1.6-4.6 mMol/g;
  iii. surface area of 2-12.6 m²/g;
  iv. insoluble in water and organic solvent; and
  v. reusable,
  said process comprises simultaneous partial carbonization and sulfonation of glycerol by reacting it with concentrated or fuming sulphuric acid, at a temperature in the range of 200-300° C., under a stream of $N_2$ gas or dry air, for a period until the reaction mixture becomes black powder, cooling the resultant black powder to a temperature of 20-30° C. and washing it with hot water until neutralization of the wash water to neutral pH, followed by washing and drying the resultant product, at a temperature of 110-130° C. to obtain the desired heterogeneous solid acid catalyst.

4. A process according to claim 3, wherein the glycerol is selected from the group consisting of technical grade glycerol, crude glycerol obtained as byproduct during biodiesel process and glycerol pitch obtained as a byproduct of fat splitting.

5. A process according to claim 3, wherein the ratio of glycerol to sulphuric acid used is in the range of 1:3 to 1:5 (w/w).

6. A process for the esterification of vegetable or animal oil free fatty acids using a glycerol based heterogeneous solid acid catalyst which comprises reacting vegetable oil or animal fat with 3-85% free fatty acid (FFA) with alcohol in the presence of solid acid catalyst, at a temperature of 35-90° C., for a period of 1-12 hours to obtain the resultant corresponding fatty acid esters, wherein the heterogeneous solid acid catalyst has the following characteristics:
  ii. molecular composition $CH_{0.53-0.87}S_{0.015-0.03}O_{0.035-0.51}$;
  iii. acid density in the range of 1.6-4.6 mMol/g;
  iv. surface area of 2-12.6 m²/g;
  v. insoluble in water and organic solvent; and
  vi. is reusable.

7. The process according to claim 6, wherein the fatty acid moiety contains any carbon atom number up to 24.

8. The process according to claim 7, wherein the alcohol is selected from methanol, ethanol and isopropanol.

9. The process according to claim 6, wherein the molar ratio of fatty acid to alcohol is in the range of 1:1 to 1:30.

10. The process according to claim 6, wherein the reaction temperature is in the range of 60-75° C.

11. The process according to claim 6, wherein the glycerol based solid acid catalyst is 2-20% of the fatty acid or free fatty acid present in the vegetable oil or animal fat feed stock.

12. The process according to claim 6, wherein the reaction time for esterification is in the range of 3-5 hours.

13. The process according to claim 6, wherein the catalyst is employed either in a batch or continuous process of esterification.

14. The process according to claim 6, wherein the catalyst is recyclable for at least 10 times without any leaching in the reaction system.

15. The process according to claim 6, wherein the % conversion of esterification of alcohol is in the range of 45-99%.

16. The glycerol based heterogeneous solid acid catalyst useful for the esterification of fatty acids as recited in claim 1, wherein the heterogeneous solid acid catalyst is insoluble in the organic solvent selected from the group consisting of chloroform, hexane, pyridine and N,N-dimethylformamide.

17. The process for the preparation of a glycerol based heterogeneous solid acid catalyst as recited in claim 3, wherein the heterogeneous solid acid catalyst is insoluble in the organic solvent selected from the group consisting of chloroform, hexane, pyridine, N,N-dimethylformamide.

18. The process for the esterification of vegetable or animal oil free fatty acids using a glycerol based heterogeneous solid acid catalyst as recited in claim 6, wherein the heterogeneous solid acid catalyst is insoluble in the organic solvent selected from the group consisting of chloroform, hexane, pyridine and N,N-dimethylformamide.

* * * * *